(12) United States Patent
Drobnik et al.

(10) Patent No.: US 7,361,135 B2
(45) Date of Patent: *Apr. 22, 2008

(54) BRACHYTHERAPY SYSTEM FOR DISPENSING MEDICATION

(75) Inventors: Christopher D. Drobnik, Wauconda, IL (US); Michael W. Drobnik, Downers Grove, IL (US)

(73) Assignee: C R Bard, Inc, Murray Hill, NJ (US)

( * ) Notice: Subject to any disclaimer, the term of this patent is extended or adjusted under 35 U.S.C. 154(b) by 116 days.

This patent is subject to a terminal disclaimer.

(21) Appl. No.: 10/924,444

(22) Filed: Aug. 24, 2004

(65) Prior Publication Data

US 2006/0063962 A1    Mar. 23, 2006

(51) Int. Cl.
*A61N 5/00* (2006.01)

(52) U.S. Cl. .................................. 600/3; 600/7
(58) Field of Classification Search .............. 600/1–8
See application file for complete search history.

(56) References Cited

U.S. PATENT DOCUMENTS

| | | | |
|---|---|---|---|
| 2,153,889 A | 4/1939 | Hames et al. | |
| 3,351,099 A | 11/1967 | Lawrence | |
| 4,402,684 A * | 9/1983 | Jessup | 604/264 |
| 4,451,254 A | 5/1984 | Dinius et al. | |
| 4,697,575 A | 10/1987 | Horowitz | |
| 4,754,745 A | 7/1988 | Horowitz | |
| 4,815,449 A | 3/1989 | Horowitz | |
| 5,460,592 A | 10/1995 | Langton et al. | |
| 5,928,130 A | 7/1999 | Schmidt | |
| 6,010,446 A | 1/2000 | Grimm | |
| 6,264,600 B1 | 7/2001 | Grimm | |
| 6,450,937 B1 | 9/2002 | Mercereau et al. | |
| 6,514,193 B2 | 2/2003 | Kaplan | |
| 6,554,760 B2 | 4/2003 | Lamoureux et al. | |
| 6,572,525 B1 | 6/2003 | Yoshizumi | |
| 6,575,890 B2 | 6/2003 | Kaplan et al. | |
| 6,616,593 B1 | 9/2003 | Elliott et al. | |
| 6,638,206 B2 | 10/2003 | Green et al. | |
| 6,723,037 B2 | 4/2004 | Hamazaki et al. | |
| 6,746,661 B2 | 6/2004 | Kaplan | |
| 6,761,680 B2 | 7/2004 | Terwilliger et al. | |
| 2002/0169354 A1 | 11/2002 | Munro, III | |
| 2002/0180096 A1 | 12/2002 | Karl et al. | |
| 2003/0084988 A1 | 5/2003 | Terwilliger et al. | |
| 2003/0088140 A1 | 5/2003 | Terwilliger et al. | |
| 2003/0088141 A1 | 5/2003 | Terwilliger et al. | |
| 2003/0088144 A1 | 5/2003 | Terwilliger et al. | |
| 2003/0092958 A1 | 5/2003 | Terwilliger et al. | |
| 2003/0097035 A1 | 5/2003 | Tucker et al. | |
| 2003/0171637 A1 | 9/2003 | Terwilliger et al. | |
| 2004/0019381 A1 | 1/2004 | Pflueger | |

OTHER PUBLICATIONS

Novel and Inexpensive System for Interstitial I125 Seed Implants, William L. DeGinder and Vitthalbhai D. Mistry, Int. J. Radiation Oncology Biol. Phys., vol. 4, pp. 745-747, Pergamon Press Inc. 1978.

* cited by examiner

Primary Examiner—John P Lacyk (57) ABSTRACT

A delivery system for interstitial radiation therapy that uses a brachytherapy needle assembly for simultaneously dispensing an effective amount of medicine, such as anti-inflammatory agents, along with radioactive seeds. Medicine can be stored in and dispensed from a reservoir attached to a needle hub or to a stylet handle or it can be injected into the needle via a three-way fitting. Alternatively, medication can be added directly to the needle cannula. Additionally, the brachytherapy needle or the radioactive seeds and spacers can be coated with medication that would be absorbed by the body upon implantation.

30 Claims, 4 Drawing Sheets

BRACHYTHERAPY SYSTEM FOR DISPENSING MEDICATION

BACKGROUND OF INVENTION

The invention relates generally to brachytherapy needles and more particularly to systems that can simultaneously dispense medication along with radioactive seeds.

Brachytherapy refers to a localized method of treating cancer that places radioactive sources directly within tissue. The advantage of brachytherapy is that very high doses of ionizing radiation are delivered to a localized area, such that the radiation is supplied primarily to the treatment area, without significantly affecting tissues throughout the body. This ability, when combined with a rapid reduction in the radiation dose as a function of distance, shields distant anatomies from unwanted radiation. Hence, the technique has provided excellent results for localized control of various tumors.

Brachytherapy commonly employs a method whereby radioactive seeds and optionally spacers, can be implanted in a designated area to treat conditions such as cancer. To treat prostate cancer, needles are inserted through the perineum into the prostate gland. Appropriate needle placement can be determined based on a dosimetry plan prepared by a physician and is commonly executed using a guiding template or grid to guide needle placement as described generally in U.S. Pat. No. 5,931,786 to Witmore, the contents of which are incorporated herein by reference. Additional details are provided in "Ultrasound Guided—Transperineal Implantation for the Treatment of Early Stage Prostate Cancer" by Grimm, Blasko and Nagle in Atlas of Urologic Clinics of North America, Vol. II, No. 2, October 1994, the contents of which are incorporated by reference.

Placement techniques of brachytherapy seeds vary, but generally, they are placed using needles containing both radioactive seeds and optionally spacers, which position the seeds and spacers in accordance with the dosimetry plan. Seeds, and sometimes seeds and spacers, are loaded into the needle cannula and the needle is inserted through the grid into the prostate gland. After the needle is properly positioned in the prostate, a stylet, having a diameter smaller than that of the needle, can be inserted into the needle behind the seeds and spacers. The needle can then be withdrawn over the stylet, which remains fixed in place. In this way, the seeds and spacers are constrained to remain in the prostate as the needle is withdrawn. This is repeated twenty to thirty times to implant a three-dimensional array of radioactive seeds. It is the intention of the physician that the seeds be positioned as precisely as possible to correspond to the three-dimensional dosimetry plan.

The use of twenty to thirty needles breaking through the skin and tissue and leaving behind foreign objects can lead to adverse reactions and trauma to the surrounding area. Trauma, bleeding and swelling to the prostate and surrounding tissue during and after a brachytherapy implant procedure can displace the seeds and lead to imprecise doses of radiation. This can involve some zones that are unintentionally, undesirably, and possibly dangerously, too hot and/or too cold.

Trauma and swelling are commonly treated by administering systemic drugs to the patient. This has the disadvantage of requiring enough drug to be dispersed throughout the body, even though the trauma and swelling are localized. This can delay the effectiveness of the drugs and can cause undesirable drug interactions and might not be suitable for all patients.

Additional known devices used to deliver seeds are disclosed in U.S. Pat. No. 4,402,308 to Scott, U.S. Pat. No. 4,697,575 to Horowitz, U.S. Pat. No. 5,860,909 to Mick, et al. and U.S. Pat. No. 5,938,583 to Grimm, which are incorporated herein by reference. Conventional devices used for storing and delivering radioactive seeds are also described in U.S. Pat. No. 4,086,914 to Moore and U.S. Pat. No. 4,167,179 to Kirsch, which are incorporated herein by reference. However, none of these references adequately disclose methods of treating and addressing the trauma and swelling that can occur at the implantation site.

Accordingly, a need exists for improved treatment of trauma and swelling to tissue caused by a brachytherapy needle implant procedure.

SUMMARY OF THE INVENTION

Generally speaking, in accordance with the invention, a brachytherapy needle is provided to dispense an effective amount of medicine, preferably an anti-inflammatory drug, at the time brachytherapy seeds are implanted. The needle would allow for the dispensing of medicines, such as anti-inflammatory agents, chemotherapy agents, clotting agents, anesthetics, steroids and the like, along with radioactive seeds, during a needle implant procedure. A needle could contain one or more drugs, chosen by the physician and would dispense the medicine simultaneously with at least one radiation source as they are ejected from the needle. Procedures in accordance with the invention would allow for the administration of medicine selected by a physician at the time of an implant procedure.

In one embodiment of the invention, a needle having a reservoir attached to the needle hub is provided wherein an effective amount of medication would be stored and dispensed into an insertion path along with the contents of the needle. In a second embodiment of the invention, the reservoir is attached to a hollow stylet of a needle assembly. In a third embodiment of the invention, a three-way fitting is attached to the needle hub and an effective amount of medication is delivered to an afflicted area by inserting a syringe or similar device loaded with medication into the fitting and ejecting the medication either before, during or after the seeds are ejected. In a fourth embodiment, a syringe loaded with medication having a plunger and a stopper adapted to receive a stylet therethrough is attached to the needle hub and an effective amount of medication is delivered to a desired location by depressing the needle plunger, causing medication to flow into the cannula and be dispensed when seeds are implanted into tissue with the use of a stylet. In a fifth embodiment, the elongated blunt needle of a syringe loaded with medication is used to take the place of the stylet. In a sixth embodiment of the invention, the stylet has a length and width small enough to fit into the needle lumen, is not round, and can be a C, X or V-shaped configuration, providing a larger cross section for the flow of medication than would a cylindrically shaped stylet with the same maximum width dimension. In a seventh embodiment of the invention, an effective amount of medication is added directly to the cannula holding the seeds. In an eighth embodiment of the invention, a seed-containing needle with at least one tab cut out of the wall of the cannula lumen is flushed through the opening at the tab, with medication of the doctor's choosing, coating the seeds with medication prior to implant. In a ninth embodiment of the invention, the needle is coated with an effective amount of medication that would be absorbed by the body upon implantation. In a tenth embodiment of the invention, the radioactive seeds and spacers are coated with an effective amount of medication that would be absorbed by the body upon implantation. In a eleventh embodiment of the invention, the needle cannula is constructed with a dual lumen such that one lumen contains the radioactive seeds and a second lumen carries an effective amount of medication. In another embodiment of the invention, an effective amount of medicine is in a medicine container, similar to the size of the seeds, and is loaded and dispensed with the radioactive seeds upon implantation.

Accordingly, it is an object of this invention to provide an improved system and method for the administration of medicine to treat trauma caused by brachytherapy techniques.

Still other objects and advantages of the invention will in part be obvious and will in part be apparent from the specification and drawings.

The invention accordingly comprises the several steps and the relation of one or more of such steps with respect to each of the others, and the system possessing the features, properties, and the relation of elements, which are exemplified in the following detailed disclosure, and the scope of the invention will be indicated in the claims.

BRIEF DESCRIPTION OF THE DRAWINGS

For a fuller understanding of the invention, reference is had to the following description, taken in connection with the accompanying drawings, in which.

The drawings are not necessarily to scale. For example, the actual stylets and needles will typically be relatively longer, compared to the diameter depicted herein. Furthermore, the stylets will typically have a relatively larger diameter, and will commonly be larger in diameter than the seeds. The seeds will typically have a relatively larger outer diameter, compared to the inner diameter of the needle cannula. Also, the size of the syringe will typically have a larger diameter compared to the needle. The relative sizing depicted was chosen to more clearly depict various aspects and details of the invention. Also, similar structures are assigned the same reference numerals.

DETAILED DESCRIPTION OF THE PREFERRED EMBODIMENTS

Figure 1:
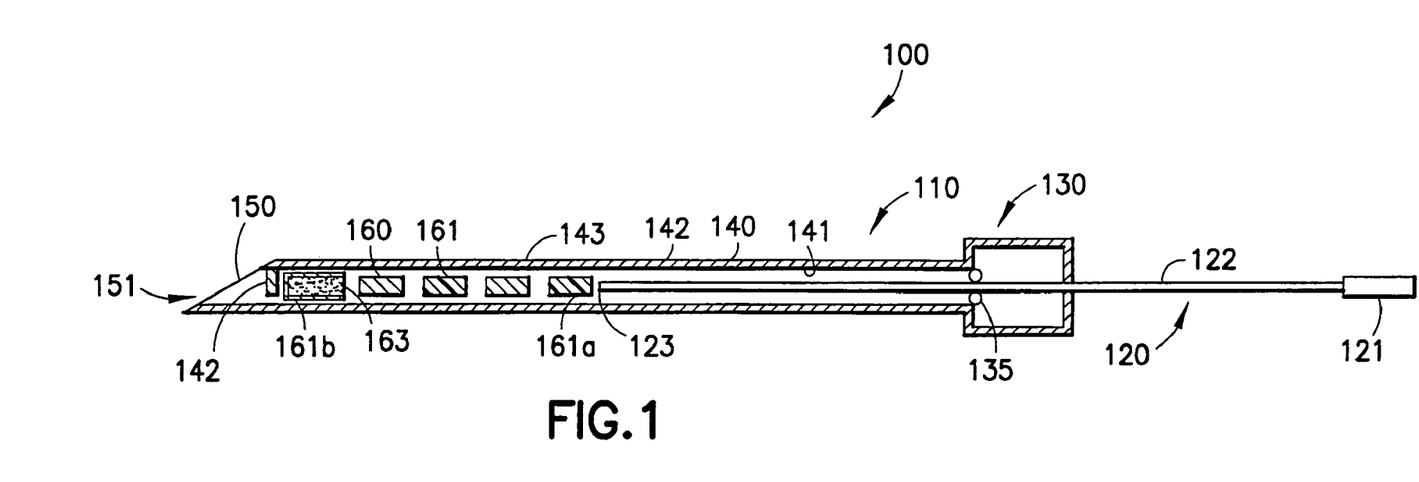
FIG. 1 is a cross-sectional view of a needle assembly in accordance with an embodiment of the invention.

A device for simultaneously delivering brachytherapy radiation sources and anti-trauma or other medicine in accordance with a preferred embodiment of the invention is shown generally as needle assembly 100 in FIG. 1. Needle assembly 100 comprises a needle 110, which is formed with a cannula shaft 140 and a distal tip section 150.

Needles in accordance with the invention are typically made from stainless steel and have an outer diameter of 1.3 mm to 1.5 mm and an inner diameter of 1.0 to 1.2. They are typically 15 cm to 25 cm in length. Tip 150 has a sharp and beveled end 151 to promote ease of insertion. An assembly of brachytherapy seeds 160 and spacers 161 are loaded into a lumen 141 of cannula 140, lumen 141 defined by an inner wall surface of needle 110. The distal end of lumen 141 can be sealed with a plug 142, which can be formed of bone wax or the like. Alternatively, a tab or other stop feature can be used to hold seeds 160 and spacers 161 within lumen 141.

Needle assembly 100 also includes a stylet 120 having a stylet shaft 122 and a stylet handle 121 at the proximal end thereof. A distal stylet tip 123 is inserted into a hub 130 at the proximal end of lumen 141 and positioned behind the last seed or in this case, a last spacer 161a. In preferred embodiments of the invention, the hub includes a fluid-sealing structure 135, to prevent liquid medication from leaking out the proximal end of the hub. To deposit seeds 160 and spacers 161, needle 110 is inserted into the desired location of the body, stylet 120 is inserted until the tip 123 contacts proximal spacer 161a (or a seed) and then held in a fixed position with respect to the patient as needle 110 is backed out of the body, leaving seeds 160 and spacers 161 behind.

In one embodiment of the invention, a distal spacer 161b, located in front of the first seed in the strand of seeds, and optionally spacers (or at any other selected location), can contain a prescribed quantity of medicine 163 or can be coated with medicine on its outside surface. Medicine containing spacer 161b should be formed of absorbable material or readily dissolving material, which will release medicine 163 stored therein. Alternatively, medicine container 161b can be in the form of a pill or capsule. In another embodiment of the invention, the interstices between seeds 160 and spacers 161 can be filled or partially filled with medication. In another embodiment of the invention, an outside surface 142 of cannula 140 can be coated with a prescribed quantity of medication 143.

Figure 2:
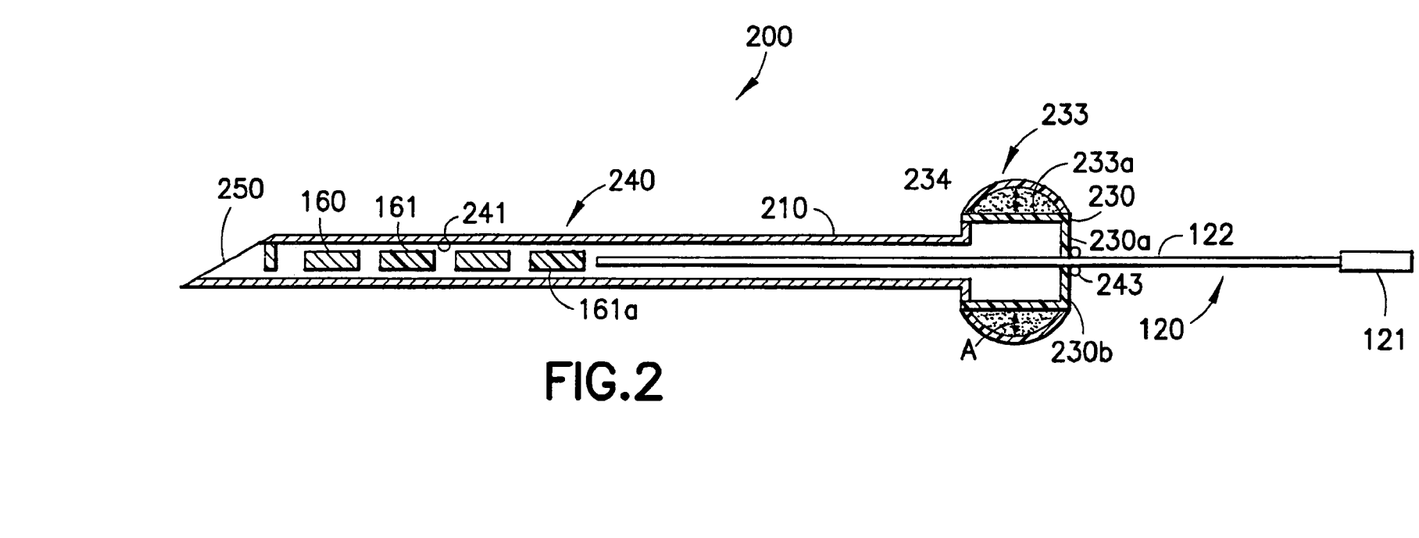
FIG. 2 is a cross-sectional view of a medicine reservoir attached to a needle hub in accordance with an embodiment of the invention.

A system for the direct delivery of medication and brachytherapy seeds to the same location in accordance with another embodiment of the invention is shown generally as a needle assembly 200 in FIG. 2. Needle assembly 200 comprises a needle 210 and stylet 120. Needle 210 is formed with a cannula shaft 240, a distal tip 250 and a proximal hub 230 for receiving the distal end of stylet 120. Hub 230 is formed with a reservoir 233 in fluid communication with a lumen 241 of cannula 240. Reservoir 233 acts as a temporary storage structure. Reservoir 233 can be in the form of an elastic bulb, such as one used for a large dropper with an elastic wall 233a. Reservoir 233 can have a volume of up to 1 ml, or larger. A seal 243 should be provided to prevent the outflow of liquids from hub 230. Reservoir 233 can be depressed, being that it is a collapsible and resilient container, and its contents released in the direction of double headed arrow A. A fluid passage (not shown) can be used to connect reservoir 233 and lumen 241. An effective amount of medication can be drawn into reservoir 233. This facilitates simultaneous delivery of a medication 234 along with seeds 160 and spacers 161 into a patient. Medicine from reservoir 233 can be dispensed as seeds 160 are being ejected, before and optionally, thereafter.

Figure 3:
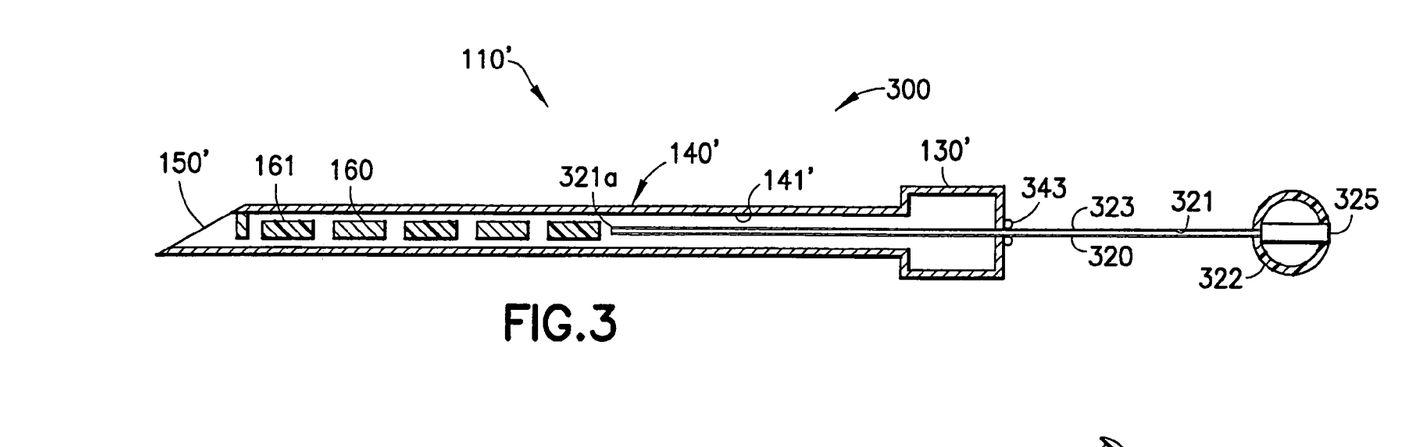
FIG. 3 is a cross-sectional view of a medicine reservoir attached to a stylet handle in accordance with an embodiment of the invention.

Another system for the direct delivery of medicine and brachytherapy seeds to the same location in accordance with an embodiment of the invention is shown generally as a needle assembly 300 in FIG. 3. Needle assembly 300 includes a needle 110', having a cannula 140' with a lumen 141', a distal tip 150' and a proximal hub 130'. It also includes a dispensing stylet 320 formed with a shaft 323 and a handle 325. A medicine reservoir 322 is attached to a stylet handle 325. Reservoir 322 is in the form of an elastic dropper bulb with a fluid passage to a stylet lumen 321. Stylet lumen 321 allows medication to pass from stylet reservoir 322, through it and be dispensed through lumen end 321a before, during or after seeds 160 and spacers 161 located in needle cannula 340 are dispensed from cannula 340. An end user or a manufacturer can draw an effective amount of medication into reservoir 322 for delivery. Reservoir 322 can be a bulb, syringe or any other similar-type structure. A seal 343 can be provided to prevent the outflow of liquids.

Figure 4:
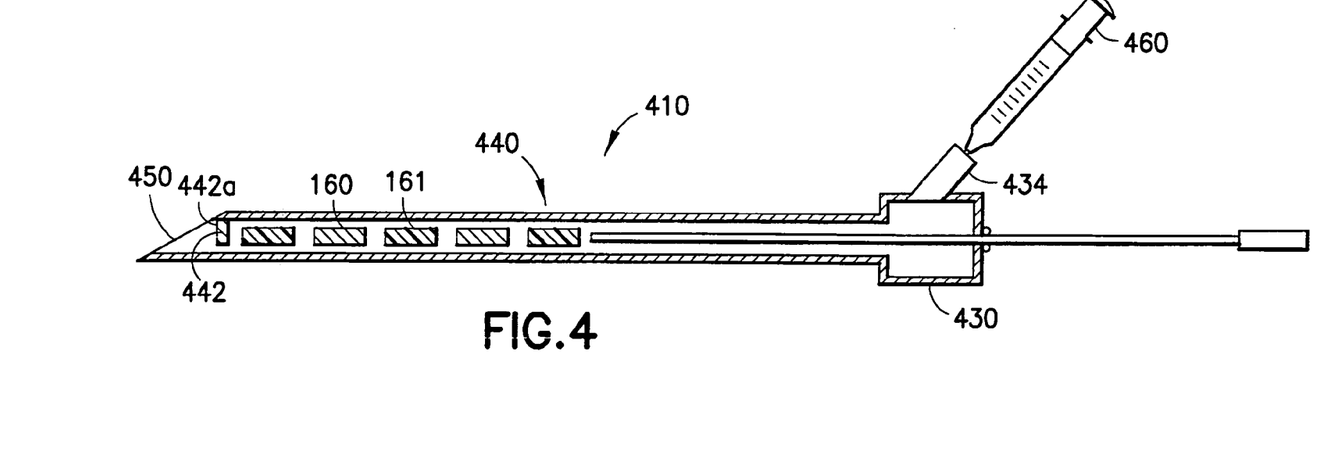
FIG. 4 is a cross-sectional view of a three-way fitting attached to a needle hub in accordance with an embodiment of the invention.

Another system for the direct delivery of medicine and brachytherapy seeds to the same location in accordance with an embodiment of the invention is shown generally as a needle assembly 400 in FIG. 4. Needle assembly 400 comprises a needle 410 formed with a cannula shaft 440. Cannula shaft 440 has a distal tip 450 and a proximal hub 430 comprising a three-way fitting 434. An effective amount of medication can be delivered to the desired location by coupling a syringe 460, or similar device loaded with medication, with fitting 434 and ejecting the medication either before, during or after seeds 460 are ejected. An effective amount of medication can also be added directly to cannula 440 holding seeds 160 and spacers 161 to be dispensed simultaneously with same.

Figure 5:
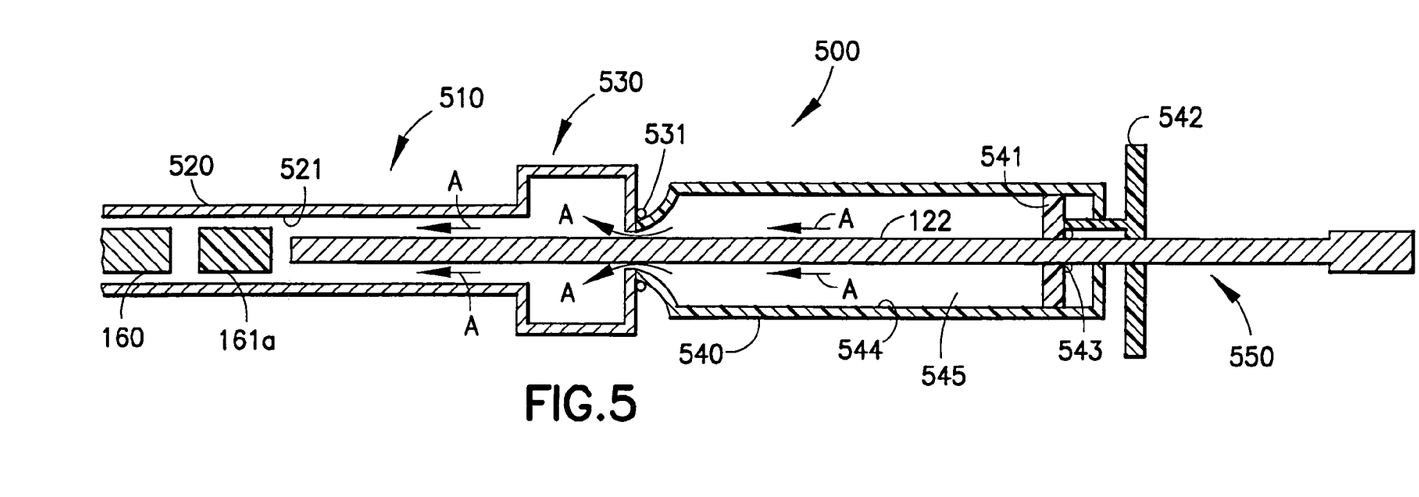
FIG. 5 is a partial cross-sectional view of a syringe joined to a needle hub adapted to receive a stylet through its plunger and stopper in accordance with an embodiment of the invention.

Still another system for the direct delivery of medicine and brachytherapy seeds to the same location in accordance with an embodiment of the invention is shown generally as a needle assembly 500 in FIG. 5. Needle assembly 500 comprises a needle 510, a syringe 540 and a stylet 550. Needle 510 is formed with a cannula shaft 520 having a proximal hub 530 for receiving syringe 540. Syringe 540 comprises a syringe barrel 544 defining a medication reservoir 545, a stopper 541 and a plunger 542, which is pressed to urge stopper 541 down barrel 544. Syringe 540 can be attached to hub 530 forming a tight seal 531 to prevent the contents of syringe barrel 544 or hub 530 from leaking out. Plunger 542 and stopper 541 contain openings to sealingly and slidingly receive a stylet 120 that passes through their structures. Stylet 550 should be fitted such that a stopper seal 543 is formed between stylet 550 and stopper 541 and the contents of syringe barrel 544 do not leak through the opening when plunger 542 is depressed. Stylet 550 runs the length of syringe 540 as well as into a lumen 521 of needle 510 so as to be able to push out radioactive seeds 160 into a desired location upon implantation. Syringe barrel 544 can contain medication chosen by a physician.

During an implantation procedure, lumen 521 of needle 510 is loaded with radioactive seeds 160 and, optionally, spacers 161. Needle 521 is inserted into a desired location and with syringe 540 attached at hub 530, plunger 542 is selectively depressed to force the medication of choice contained in reservoir 545 of syringe barrel 544 to flow in the direction of arrow A into lumen 521. To dispense seeds, stylet 550 is held in place by grasping handle 121 and needle 510 is pulled back, with stopper 541 and plunger 542 sliding over stylet 550, leaving seeds 160 and the medication behind in the afflicted tissue.

In one embodiment of the invention, stylet 550 is joined (either permanently or via friction) to plunger 542, to enable co-dispersing of seeds and medication in one motion. The cross-sectional area of barrel 544 should be sized to dispense a selected amount of medication as stylet 550 is moved to dispense seeds and thereby control the amount of dispensed medication.

Figure 6:
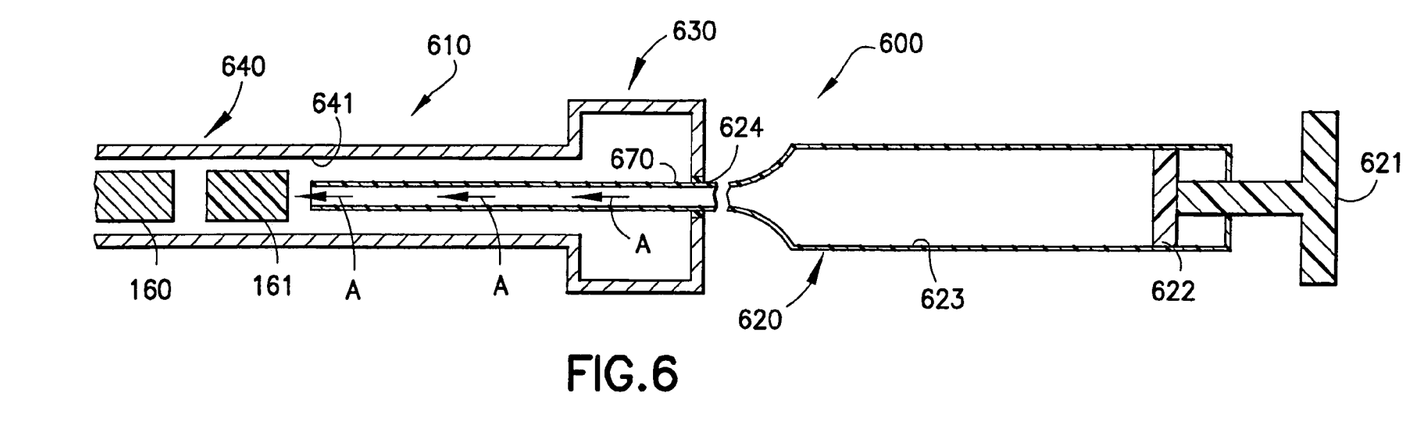
FIG. 6 is a cross-sectional view of a syringe having a stylet-like elongated needle in accordance with an embodiment of the invention.

Direct delivery of medicine and brachytherapy seeds to the same location in accordance with an embodiment of the invention can also be accomplished by the system shown generally as a needle assembly 600 in FIG. 6. Needle assembly 600 comprises a needle 610 sealingly attached to a syringe 620. Needle 610 is formed with a cannula shaft 640 having a proximal hub 630 for receiving a stylet-like, preferably blunt needle 670 of syringe 620. The cannula shaft has a lumen 641, which holds radioactive seeds 160, and, optionally, spacers. Blunt needle 670 is sized to extend through lumen 641 to the distal end of needle 610. Syringe 620 comprises a syringe barrel 623, a plunger 621 and a stopper 622. Syringe 620 forms a seal 624 when medication dispensing stylet-like needle 670 is disposed in needle 610. Seal 624 prevents any leakage of the contents of syringe 620.

Any medication chosen by a treating physician can be stored in syringe barrel 623. When the treating physician is ready to implant radioactive seeds 160 into a desired location, the physician can depress plunger 621 moving stopper 622 forward and forcing the medication in syringe barrel 623 to flow in the direction of arrows A. To dispense seeds, needle 610 is backed out of the patient, while syringe 620 is held in a fixed position relative to the patient.

Figure 7:
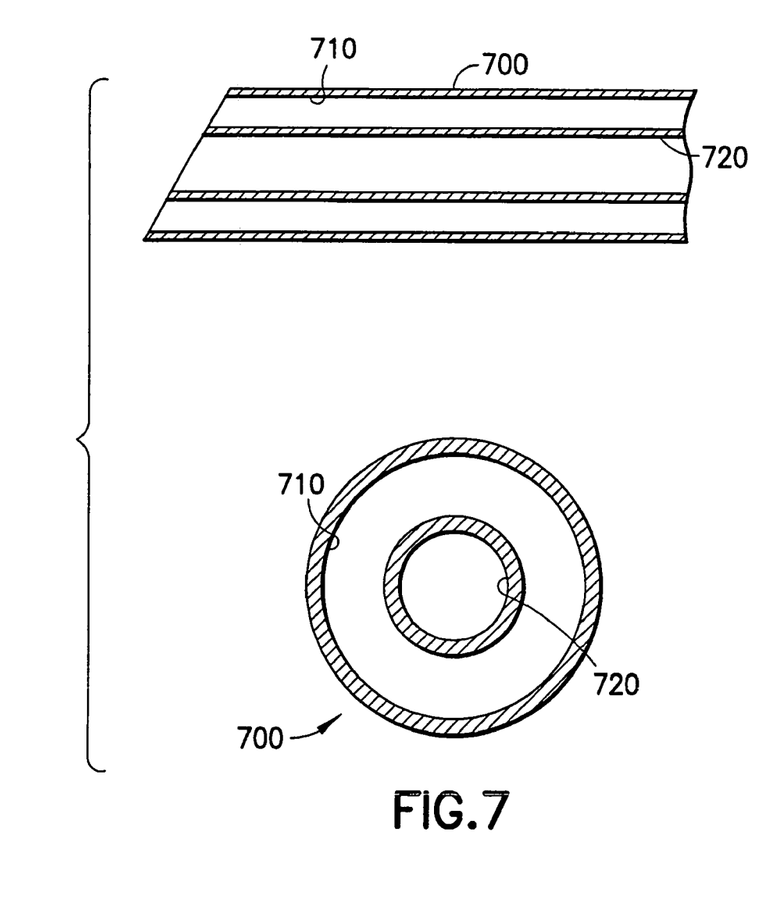
FIG. 7 is a frontal view of a dual lumen cannula in accordance with an embodiment of the invention.

Another system for the direct delivery of medicine and brachytherapy seeds to the same location in accordance with an embodiment of the invention is shown generally as dual lumen cannula in FIG. 7. Needle cannula 700 can be constructed with a dual lumen such that an inner lumen 720 contains at least one radioactive source and an outer lumen 710 is in fluid communication with a reservoir storing medication. Upon implantation, the contents of inner lumen 720 and outer lumen 710 are dispensed simultaneously or sequentially. The medication can be ejected from outer lumen 710 by squeezing a coupled bulb or by advancing a plunger.

Figure 8:
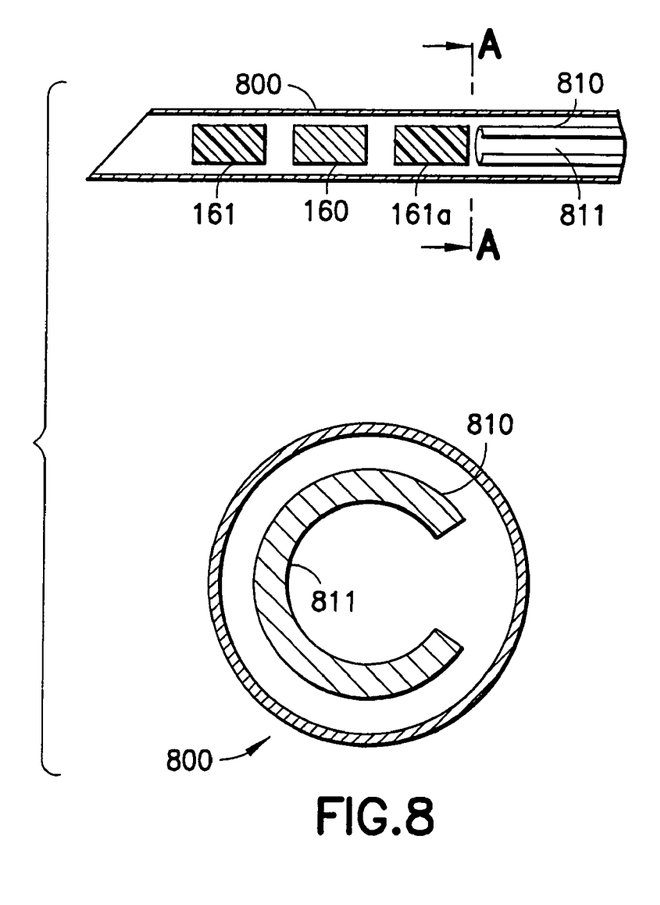
FIG. 8 is a frontal view of a flow enhancing stylet in accordance with an embodiment of the invention.

Another system for the direct delivery of medicine and brachytherapy seeds to the same location in accordance with an embodiment of the invention is shown generally as a grooved stylet in FIG. 8. In a needle assembly, a stylet 810 having a groove 811 formed along the length of the stylet is used. Other non-cylindrical stylet shapes such as an X, a V or a rectangle are acceptable, so long as they permit a relatively large cross-sectional area for fluid medication to flow while maintaining sufficient structural integrity to hold their own shape and supply the force necessary to eject the seeds. Grooved stylet 810 can be used with various embodiments of the invention by providing groove 811 increasing the volume inside a cannula 800 for medication prior to implantation, such as the embodiments shown in FIG. 2 or 4.

In some instances, a needle may have a stop feature to keep the contents of the needle from falling out. Preferably, the stop feature is a U-shaped tab configuration cut out from the needle cannula wall, such as stop feature 442a as shown in FIG. 4. This provides an opening at the distal end of the cannula and medication chosen by the attending physician can be flushed into the needle over the seeds in the cannula, coating the seeds.

Suitable anesthetics that can be used include but are not limited to amide-linked anesthetics such as lidocaine (Xylocaine®), mepivacaine (Carbocaine®), etidocaine (Duranest®), dibucaine (Nupercainal®) and prilocaine (Citanest®), and ester linked anesthetics such as procaine (Novocaine®) and tetracaine (Pontocaine®).

Suitable anti-inflammatory agents that can be used include but are not limited to Ibuprofen (Motrin®, Advil®), Naproxen (Naprosyn®, Alleve®), Valdecoxib (Bextra®), Floctafenine (Idarac®), Ketoprofen (Orudis®, Oruvail®), Mefenamic Acid (Ponstel®), Nabumetone (Relafen®), Indomethacin (Indocin®), Diclofenac (Cataflam® and Voltaren®), Diflunisal (Dolobid®), Sulindac (Clinoril®), Flurbiprofen (Ansaid®), Oxaprozin (Daypro®), Fenoprofen (Nalfon®), Meclofenamate (Meclomen®), Etodolac (Lodine®), Piroxicam (Feldene®), Phenylbutazone (Cotylbutazone®), Tolmetin (Tolectin®), Meloxicam (Mobic®), Ketorolac (Toradol®), Nabumetone (Relafen®), Sulindac (Clinoril), Celecoxib (Celebrex®) and Rofecoxib (Vioxx®).

Suitable chemotherapy drugs that can be used include but are not limited to alkylating drugs such as cyclophosphamide, antimetabolites such as 5-fluorouracil (5-FU), antitumor antibiotics such as doxorubicin and bleomycin, plant alkaloids such as vinblastine and vincristine and steroid hormones such as tamoxifen.

Suitable seeds can be of various types having low energy and low half-life such as Iodine seeds, known as I-125 seeds, consisting of a welded titanium capsule containing iodine 125 absorbed on a silver rod, or Palladium 103 seeds. Additionally, seeds can be manufactured using iridium 192, cesium 131, gold 198, yttrium 90 and phosphorus 32. Other types of seeds can be used such as those described in U.S. Pat. No. 6,248,057 to Mavity et al., which patent is incorporated herein by reference. Suitable spacers can be made of bioabsorbable polymers.

One method for performing a brachytherapy procedure comprises inserting a brachytherapy needle to a desired location in a patient along an insertion path. The insertion path extends from a proximal initial insertion point to a distal needle endpoint. Once the needle is inserted, at least one radiation source is dispensed from the brachytherapy needle to a location in the insertion path. Along with the radiation source, medication is dispensed from the brachytherapy needle to a location in the insertion path before the brachytherapy needle is removed from the insertion path.

It will thus be seen that the objects set forth above, among those made apparent from the preceding description, are efficiently attained and since certain changes may be made in the above construction without departing from the spirit and scope of the invention, it is intended that all matter contained in the above description or shown in the accompanying drawings shall be interpreted as illustrative and not in a limiting sense.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

It is also to be understood that the following claims are intended to cover all of the generic specific features of the invention herein described and all statements of the scope of the invention which, as a matter of language, might be said to fall there between.

What is claimed is:

1. A method of performing a brachytherapy procedure, comprising:
    inserting a brachytherapy needle to a desired location in a patient along an insertion path extending from a proximal initial insertion point to a distal needle endpoint, wherein one or more radiation sources are loaded into a lumen of the brachytherapy needle;
    dispensing at least one radiation source of the one or more radiation sources from the distal needle endpoint of the brachytherapy needle to a location in the insertion path; and
    dispensing medication from a reservoir and through the distal needle endpoint of the brachytherapy needle to a location in the insertion path before the brachytherapy needle is removed from the insertion path, wherein the reservoir is in fluid communication with the lumen of the brachytherapy needle.

2. The method of claim 1, wherein the medication comprises an anti-inflammatory material.

3. The method of claim 1, wherein the medication comprises an anesthetic.

4. The method of claim 1, wherein at least two radiation sources of the one or more radiation sources are dispensed before the needle is removed and at least some of the medication is dispensed into the insertion path after the first radiation source is dispensed but before the last radiation source is dispensed.

5. The method of claim 1, wherein the needle comprises a lumen defined by an inner wall surface of the needle, with at least one radiation source within the lumen, the outer dimension of the radiation source being smaller than the inner dimension of the lumen, so that fluid can pass between the source and the inner wall surface and at least some of the medication is dispensed by being forced past the source between the source and the inner wall surface of the needle.

6. The method of claim 1, wherein the needle comprises the reservoir;
    wherein the reservoir is attached to a needle hub and the medication is dispensed from the reservoir, through the hub, to the lumen.

7. The method of claim 1, and wherein a hollow stylet is attached to the reservoir and medication is dispensed through the stylet and radiation sources are dispensed by moving the needle relative to the stylet.

8. The method of claim 6, wherein the needle comprises a three-way fitting attached to a needle hub and medication is dispensed from the reservoir through the three-way fitting, to the lumen.

9. The method of claim 8, wherein a syringe is coupled to the fitting and acts as the reservoir.

10. The method of claim 6, wherein a syringe loaded with medication is attached to the needle hub, the syringe having a plunger and a stopper adapted to receive a stylet therethrough and radiation sources are dispensed by moving the needle relative to the stylet and medication is dispensed by moving the plunger relative to the needle.

11. The method of claim 7, wherein the hollow stylet comprises a syringe having an elongated blunt needle, and at least one of the syringe and the elongated blunt needle is loaded with medication.

12. The method of claim 6, wherein a stylet having a C, X or V shape is used to provide increased spaced between the stylet and inner wall of the needle for the of medication.

13. The method of claim 1, wherein the needle comprises a lumen bounded by a wall, the wall is perforated so as to form a tab that descends into the lumen, and medication for coating the sources is flushed into the lumen, through the opening at the tab, prior to implanting the sources.

14. The method of claim 1, including coating the needle with medication.

15. The method of claim 1, wherein the lumen is a dual lumen and one lumen contains at least one radioactive source and a second lumen is in fluid communication with the reservoir.

16. The method of claim 1, wherein the reservoir is in the form of a collapsible, resilient container and medication is dispensed by squeezing the container.

17. A brachytherapy system, comprising:
a brachytherapy needle having a cannula with a proximal end and a distal end and a lumen defined by an inner wall surface, the lumen sized to receive radiation sources and adapted to implant those sources through the distal end at a desired location within a patient; and
a medication dispensing structure, comprising a reservoir constructed to store liquid medication in fluid communication with the lumen; whereby the system is constructed and arranged to dispense both medication and radiation sources to the same location in the patient, through the distal end, without removing the needle from the patient.

18. The brachytherapy system of claim 17, wherein the reservoir contains medication comprising anti-inflammatory material.

19. The brachytherapy system of claim 17, wherein the reservoir contains medication comprising anesthetic.

20. The brachytherapy system of claim 17, wherein the needle has a proximal hub and the reservoir is attached to the hub.

21. The brachytherapy system of claim 17, comprising a hollow stylet sized to fit within the lumen so that sources can be dispensed by moving the needle relative to the stylet, wherein the reservoir is joined to the hollow stylet and is in fluid communication with the hollowed portion of the stylet to dispense medication through the stylet.

22. The brachytherapy system of claim 17, wherein the system comprises a syringe loaded with medication attached to the proximal end of the needle, the syringe having a plunger and a stopper and a stylet disposed through a sealed opening in the stopper and also extending proximally past the plunger and into the lumen.

23. The brachytherapy system of claim 17, wherein the system comprises a syringe having an elongated needle loaded with medication, the syringe needle sized to extend through the lumen to the distal end of the needle and act as a stylet.

24. The brachytherapy system of claim 20, wherein the needle has a three-way fitting attached to the needle hub and the reservoir is in fluid communication with the lumen.

25. The brachytherapy system of claim 17, wherein the needle has at least one tab cut out of the needle cannula wall and medication is flushed into the lumen and through the opening in the tab.

26. The brachytherapy system of claim 17, wherein the needle is coated with medication.

27. The brachytherapy system of claim 17, wherein the lumen is a dual lumen and one lumen contains at least one radioactive source and a second lumen is in fluid communication with a reservoir storing medication.

28. The brachytherapy system of claim 17, wherein the system comprises a stylet having a length and width small enough to fit into the lumen, the stylet having a non-circular cross-section, providing a larger cross-section for the flow of medication than would a cylindrically shaped stylet with the same maximum width dimension.

29. The brachytherapy system of claim 28, wherein the stylet has an X shaped configuration.

30. The brachytherapy system of claim 28, wherein the stylet has a V or C shaped configuration.

* * * * *

UNITED STATES PATENT AND TRADEMARK OFFICE
CERTIFICATE OF CORRECTION

PATENT NO. : 7,361,135 B2  Page 1 of 1
APPLICATION NO. : 10/924444
DATED : April 22, 2008
INVENTOR(S) : Drobnik et al.

It is certified that error appears in the above-identified patent and that said Letters Patent is hereby corrected as shown below:

Column 6, line 60, "FIG." should be changed to -- FIGS. --.

Claim 13, line 5, "sources" should be changed to -- at least one source --.

Signed and Sealed this

Nineteenth Day of May, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,361,135 B2 | Page 1 of 1 |
| APPLICATION NO. | : 10/924444 | |
| DATED | : April 22, 2008 | |
| INVENTOR(S) | : Drobnik et al. | |

It is certified that error appears in the above-identified patent and that said Letters Patent is hereby corrected as shown below:

Column 6, line 60, "FIG." should be changed to -- FIGS. --.

Column 9, Claim 13, line 5, "sources" should be changed to -- at least one source --.

This certificate supersedes the Certificate of Correction issued May 19, 2009.

Signed and Sealed this

Ninth Day of June, 2009

JOHN DOLL
*Acting Director of the United States Patent and Trademark Office*